(12) United States Patent
Nakanishi et al.

(10) Patent No.: US 10,022,659 B2
(45) Date of Patent: Jul. 17, 2018

(54) DEVICE FOR ISOLATING PERIPHERY CIRCULATING TUMOR CELLS OR RARE CELLS, AND METHOD OF ISOLATING PERIPHERY CIRCULATING TUMOR CELLS OR RARE CELLS

(71) Applicants: AICHI PREFECTURE, Nagoya-shi, Aichi (JP); OPTNICS PRECISION CO., LTD., Ashikaga-shi, Tochigi (JP)

(72) Inventors: Hayao Nakanishi, Aichi (JP); Seiji Ito, Aichi (JP); Seichin Kinuta, Tochigi (JP); Yoshiyuki Ichinosawa, Tochigi (JP); Akiko Yusa, Aichi (JP); Hiroyuki Honda, Aichi (JP); Mina Okochi, Aichi (JP)

(73) Assignees: AICHI PREFECTURE, Nagoya-shi, Aichi (JP); OPTNICS PRECISION CO., LTD., Ashikaga-shi, Tochigi (JP)

(*) Notice: Subject to any disclaimer, the term of this patent is extended or adjusted under 35 U.S.C. 154(b) by 406 days.

(21) Appl. No.: 14/407,466

(22) PCT Filed: Jul. 23, 2014

(86) PCT No.: PCT/JP2014/069469
§ 371 (c)(1),
(2) Date: Dec. 11, 2014

(87) PCT Pub. No.: WO2015/012315
PCT Pub. Date: Jan. 29, 2015

(65) Prior Publication Data
US 2016/0136552 A1    May 19, 2016

(30) Foreign Application Priority Data
Jul. 24, 2013    (JP) .................................. 2013-153717

(51) Int. Cl.
*G01N 33/49* (2006.01)
*A61M 1/34* (2006.01)
(Continued)

(52) U.S. Cl.
CPC ............... *B01D 39/10* (2013.01); *A61M 1/34* (2013.01); *A61M 1/36* (2013.01); *B01D 37/00* (2013.01);
(Continued)

(58) Field of Classification Search
CPC .......... B01D 39/10; B01D 37/00; A61M 1/34; G01N 33/491
See application file for complete search history.

(56) References Cited

U.S. PATENT DOCUMENTS

| 2004/0072278 A1* | 4/2004 | Chou ..................... G01N 35/00 |
| | | 435/29 |
| 2007/0025883 A1* | 2/2007 | Tai .......................... B01D 61/14 |
| | | 422/400 |

(Continued)

FOREIGN PATENT DOCUMENTS

| CN | 202730123 U | 2/2013 |
| JP | 2005-10177 A | 1/2005 |

(Continued)

OTHER PUBLICATIONS

Extended European Search Report dated May 31, 2016, issued in corresponding EP Patent Application.
(Continued)

*Primary Examiner* — Paul Sang Hwa Hyun
(74) *Attorney, Agent, or Firm* — SOLARIS Intellectual Property Group, PLLC

(57) ABSTRACT

A device for isolating periphery circulating tumor cells or rare cells includes a metal filter having depressions that can capture periphery circulating tumor cells or rare cells that
(Continued)

are in a body fluid, and pores that are formed at the depressions and that can pass therethrough body fluid cells other than periphery circulating tumor cells or rare cells.

8 Claims, 25 Drawing Sheets

(51) Int. Cl.
  *B01D 39/10* (2006.01)
  *A61M 1/36* (2006.01)
  *B01D 37/00* (2006.01)
  *B03C 1/02* (2006.01)
(52) U.S. Cl.
  CPC ........... *B03C 1/02* (2013.01); *A61M 2205/33* (2013.01); *G01N 33/491* (2013.01)

(56) References Cited

U.S. PATENT DOCUMENTS

| | | | | |
|---|---|---|---|---|
| 2009/0188864 | A1* | 7/2009 | Zheng | B01D 61/18 210/641 |
| 2012/0141562 | A1 | 6/2012 | Achneck et al. | |
| 2013/0330721 | A1* | 12/2013 | Tang | B01D 29/00 435/6.11 |
| 2014/0299539 | A1* | 10/2014 | Takai | B01D 39/10 210/506 |

FOREIGN PATENT DOCUMENTS

| | | |
|---|---|---|
| JP | 2007-525642 A | 9/2007 |
| JP | 3142031 U | 6/2008 |
| JP | 2009-106936 A | 5/2009 |
| JP | 2010-110272 A | 5/2010 |
| JP | 2011-163830 A | 8/2011 |
| JP | 2013-501574 A | 1/2013 |
| JP | 2013-42689 A | 3/2013 |
| KR | 2012-0042515 A | 5/2012 |
| WO | 2013/054786 A1 | 4/2013 |

OTHER PUBLICATIONS

Yusa, Akiko et al., "Isolation of Living Circulating Tumor Cells (CTCs) from Peripheral Blood Using Size-based Device and Its Application to CTC Biology in Mice", IEEE, 2013 International Symposium on Micro-NanoMechatronics and Human Science (MHS), Nov. 2013, pp. 1-3 (Japan).

Yusa, Akiko et al., "Development of a New Rapid Isolation Device for Circulating Tumor Cells (CTCs) Using 3D Palladium Filter and Its Application for Genetic Analysis", PLOS ONE, Feb. 2014, vol. 9, No. 2, Article e88821, p. 1-11 (U.S.).

English language translation of the following: Office action dated Oct. 27, 2015 from the SIPO in a Chinese patent application corresponding to the instant patent application.

Isolation of rare circulating tumour cells in cancer patients by microchip technology. Sunitha Nagrath et al. Nature, 2007, 450: 1235-1239.

F. Farace et al., Br. J. Cancer, 2011, 105: 847-853.

* cited by examiner

DEVICE FOR ISOLATING PERIPHERY CIRCULATING TUMOR CELLS OR RARE CELLS, AND METHOD OF ISOLATING PERIPHERY CIRCULATING TUMOR CELLS OR RARE CELLS

TECHNICAL FIELD

The present invention relates to a device for isolating periphery circulating tumor cells or rare cells (hereinafter also simply called "CTC isolating device") that is equipped with a specific, porous, metal filter (hereinafter also simply called "CTC isolating filter"), for isolating periphery circulating tumor cells (hereinafter also called "CTCs") or rare cells that are within a body fluid.

The present invention further relates to a method of isolating periphery circulating tumor cells or rare cells from a body fluid, that includes isolating CTCs or rare cells from a body fluid such as blood or the like of a cancer patient by using the device.

BACKGROUND ART

Tumor cells or cancer cells that circulate within the blood of a cancer patient are called CTCs. CTCs are thought to be a cause of metastatic cancers, and it has been suggested that CTC detection may be effective in early diagnosis of metastatic cancers. However, CTCs are one type of rare cell, and there are extremely few CTCs within blood, and there is, for example, approximately one CTC per from $10^8$ to $10^9$ blood cell components. Therefore, several methods of isolating CTCs have been proposed. For example, a method using a microfluidic device that binds a capture antibody to magnetic particles, that have immobilized anti-EpCAM (epithelial cell adhesion molecule) antibody, or to the resin surfaces of columnar structures or the like, a method of isolating by using a filter and by utilizing the difference in sizes of CTCs and blood cells, and the like are known as isolating methods (Isolation of rare periphery circulating tumor cells in cancer patients by microchip technology. Sunitha Nagrath et al. Nature, 2007, 450: 1235-1239), (Japanese Patent Application Laid-Open (JP-A) No. 2011-163830, JP-A No. 2013-42689, JP-A No. 2005-10177, Japanese Patent National Publication No. 2007-525642, JP-A No. 2009-106936).

A microfilter in which the material of the filter is formed of a polymer such as parylene (US Patent Application Publication No. 2011/0111412 A1) or polycarbonate (F. Farace et al., Br. J. Cancer, 2011, 105: 847-853) or the like, or silicon, a metal (JP-A No. 2013-42689), or the like, and that has on the surface thereof numerous pores of from 7 to 10 μm, is used in CTC isolating methods that use a filter. In principle, the filter has a pore size that is such that blood cells are passed therethrough and CTCs are captured on the filter.

In the metal filter disclosed in JP-A No. 2013-42689, a preferred metal is selected from gold, silver, copper, aluminum, tungsten, nickel, chromium, stainless steel and alloys thereof, and further, preferably, the length of the short side of the through-hole is from 5.0 to 15.0 μm, and the average opening ratio is from 0.1 to 50%, and the thickness of the filter is from 3 to 100 μm. In the Examples thereof, a nickel filter (average opening ratio: 1.4%, size of pore: 8×30 μm, shape of pore: rounded rectangular) is used and recovers human small cell lung cancer cell lines that have spiked within the blood. In the experiments thereof, it is stated that the cancer cell recovery rate is 74.9±10.5%, and the residual white blood cell count is 697±84.

SUMMARY OF INVENTION

Technical Problem

Size-selective CTC enrichment devices using filters such as those disclosed in the above-described background art have the advantages of being simple and low-cost and the like as compared with magnetic bead methods. However, a pre-treatment of hemolyzing blood that is the specimen is needed, and, because a pump is used as the driving force of the filter, cell stress is applied to the CTCs, and single cell sorting of living cells is difficult because of the fixing of cells and the closed nature of the flow path.

In consideration of the above-described circumstances, an object of the present invention is to achieve highly-efficient recovery of CTCs or rare cells that are living, and further, to enable single living cell sorting that is simple and gentle.

Solution to Problem

The present invention encompasses the following characteristics.

[1] A device for isolating periphery circulating tumor cells or rare cells, comprising: a metal filter having depressions that can capture periphery circulating tumor cells or rare cells that are in a body fluid; and pores that are formed at the depressions and that can pass therethrough body fluid cells other than the periphery circulating tumor cells or the rare cells.

[2] The device for isolating periphery circulating tumor cells or rare cells of [1], wherein a metal material of the filter comprises palladium or a palladium/nickel alloy.

[3] The device for isolating periphery circulating tumor cells or rare cells of [1] or [2], wherein a diameter of the depressions is from 20 to 30 μm, and a depth of the depressions is from 5 to 15 μm.

[4] The device for isolating periphery circulating tumor cells or rare cells of any one of [1] through [3], wherein a diameter of the pores is from 7 to 10 μm.

[5] The device for isolating periphery circulating tumor cells or rare cells of any one of [1] through [4], wherein a pore density of the depressions and the pores is from $1\times10^4$ to $2\times10^5$ per 1 $cm^2$.

[6] The device for isolating periphery circulating tumor cells or rare cells of any of [1] through [5], wherein a thickness of the metal filter is from 10 to 40 μm.

[7] The device for isolating periphery circulating tumor cells or rare cells of any of [1] through [6], comprising a filter cassette for setting of the metal filter.

[8] A method of isolating periphery circulating tumor cells or rare cells, comprising: injecting, into the device for isolating periphery circulating tumor cells or rare cells of any of [1] through [7], a body fluid selected from blood, stomach fluid or peritoneal washing fluid of a cancer patient; and capturing the periphery circulating tumor cells or the rare cells that are in the body fluid in the depressions of the metal filter, and thereafter, recovering the periphery circulating tumor cells or the rare cells while living.

[9] The method of isolating periphery circulating tumor cells or rare cells of [8], further comprising specifically staining the periphery circulating tumor cells or rare cells.

[10] The method of isolating periphery circulating tumor cells or rare cells of [8] or [9], comprising diluting or carrying out a pre-treatment on the body fluid.

[11] The method of isolating periphery circulating tumor cells or rare cells of [10],
wherein the pre-treatment includes: mixing the body fluid together with cationic liposomes containing magnetic nanoparticles; causing the magnetic nanoparticles to be taken into the periphery circulating tumor cells or the rare cells and white blood cells that are in the body fluid; and thereafter, causing a mixture to flow into a flow path that passes through the metal filter, and removing, from the body fluid, cells such as red blood cells and the like that did not take-in the magnetic nanoparticles by a magnet disposed before the metal filter.

Advantageous Effects of Invention

In accordance with the present invention, highly-efficient recovery of CTCs or rare cells that are living is achieved, and further, single living cell sorting that is simple and gentle can be made possible.

DESCRIPTION OF EMBODIMENTS

Embodiments of the present invention are described in detail.

1. Metal Filter that Isolates Periphery Circulating Tumor Cells (CTCs) or Rare Cells "CTC" in the present specification is a periphery circulating tumor cell that is included in the blood of a cancer patient, and means a cell that is rare and has an extremely low number of cells as compared with body fluid cells such as blood cells or the like.

"Rare cell" in the present specification means a rare tumor cell ("rare cancer cell") that is included in a body fluid such as stomach fluid, peritoneal washing fluid, lymph fluid, spinal fluid or the like of a cancer patient.

A metal filter 17 of the present embodiment is a porous metal filter in which an extremely large number of pores (pore density $1\times10^4/cm^2$ or more) are formed uniformly or regularly in an extremely thin plate that is formed from a specific metal. Conventional, publicly known CTC isolating filters are formed from resins (or polymers) such as parylene, polycarbonate and the like, and silicon. In contrast, the CTC isolating filter of the present embodiment is the metal filter 17, and has excellent characteristics that are described hereinafter and that differ from those of resin filters and the like.

Figure 4A:
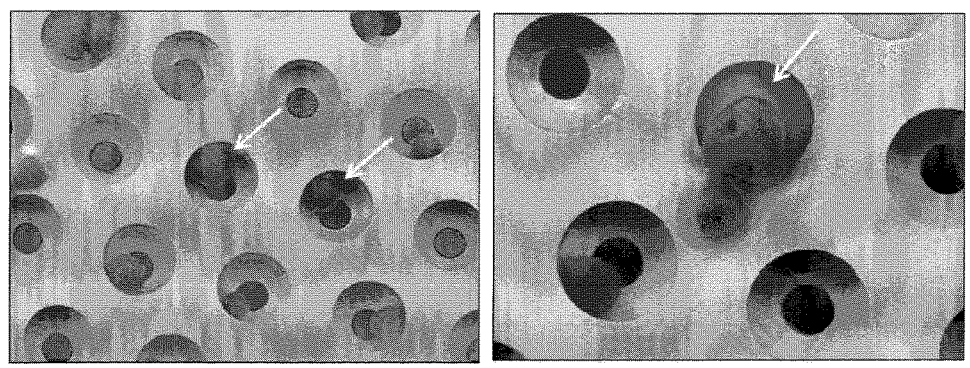
FIG. 4A is SEM images of a 3D filter that has captured cancer cells (the arrows) in the depressions (the right is an enlarged image of the left).
Figure 4B:
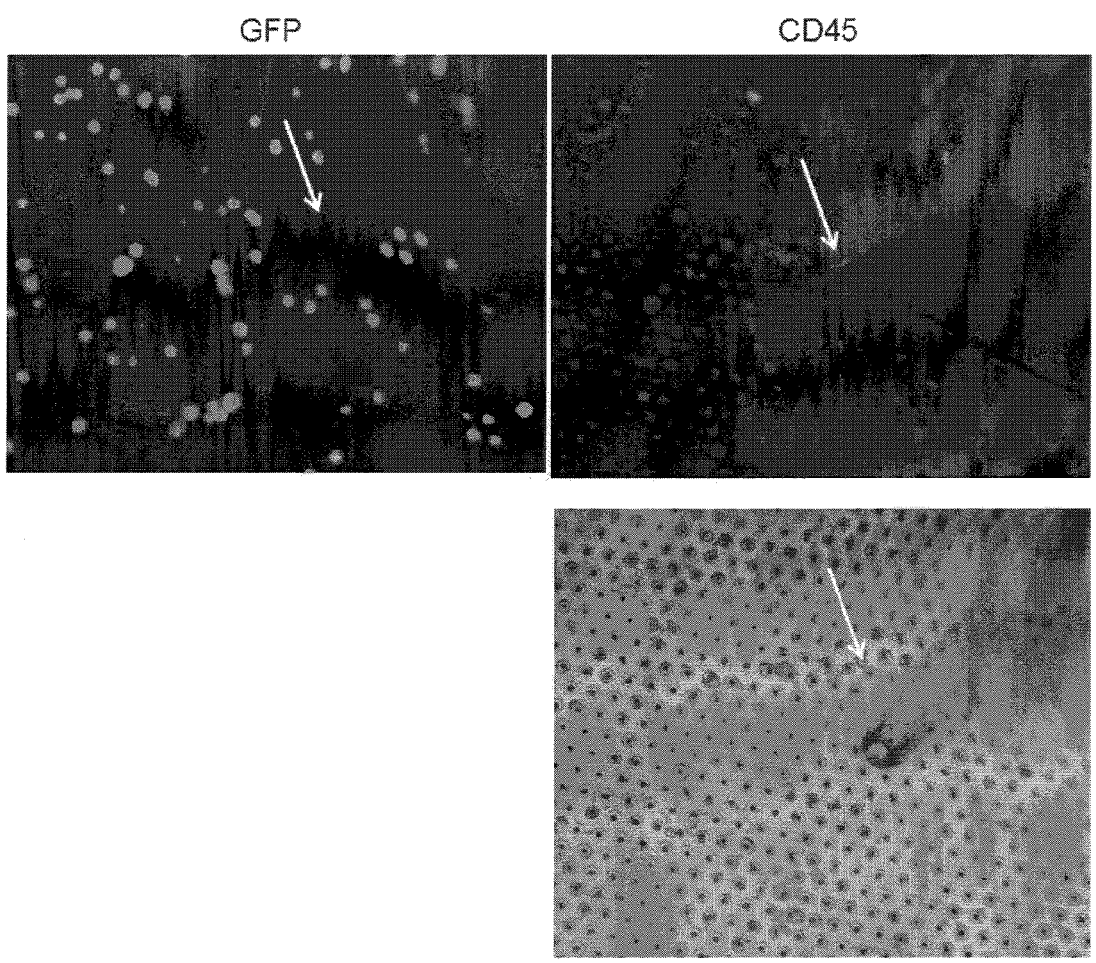
FIG. 4B A sample, that was prepared by mixing 500 cultured cancer cells (COLM5-EGFP) in 2 mL of 10 times diluted healthy human blood and diluting the mixture 10 times by PBS, was filtered by a 3D Pd/Ni filter (depression diameter 30 μm, depression depth 10 μm, pore diameter 8 μm, pore density 99,178/cm², staggered lattice array), and the cells were stained with PE-labeled anti-CD45 antibody. The upper left is a GFP fluorescence image (cancer cell detection), and the upper right is a stain image (white blood cell detection) of the PE-labeled anti-CD45 antibody. Only a few white blood cells were observed, and an image in which a cancer cell and a white blood cell both existed in a same depression was not observed. The lower right is a bright field image at the time of operating a manipulator (glass capillary) manually on a filter cassette and performing single cell sorting of a cancer cell. The arrow is the manipulator.

The material of the metal filter 17 includes at least one of, for example, palladium (Pd), platinum (Pt), gold (Au), silver (Ag), iridium (Ir), rhodium (Rh) or ruthenium (Ru). This material may be a single metal of palladium (Pd), platinum (Pt), gold (Au), silver (Ag), iridium (Ir), rhodium (Rh) or ruthenium (Ru), or may be, for example, a palladium (Pd)/nickel (Ni) alloy, a platinum (Pt)/nickel (Ni) alloy, or a gold (Au)/nickel (Ni) alloy, or the like. In the case of an alloy, preferably, the ratio of the aforementioned metal with respect to the partner metal such as nickel or the like is large. As compared with a metal such as Nickel (Ni) or the like for example, the toxicity of these metals with respect to cells such as CTCs, rare cells and the like is extremely low (FIG. 1). The reasons for this are that the toxicity of palladium (Pd) itself is low, and elution of nickel (Ni) can be prevented by an alloy of Pd and nickel (Ni) forming a solid solution. Among these, palladium or a palladium (Pd)/nickel (Ni) alloy is preferable from the standpoints of the cost of the metals and low toxicity. In the case of a Pd/Ni alloy, an alloy in which Pd exceeds 50% (by weight), e.g., an alloy of 80% Pd and 20% Ni, is preferable. The metal filter of the present embodiment, that is a Pd and Ni alloy filter, or a Pd filter or the like, is acid-resistant and heat-resistant, and various types of staining such as by the FISH method or the like are possible with the filter as is, and examination by microscope with the filter as is (upright) is possible. Further, the filter has high hardness and high durability, and it is difficult for cells to adhere thereto even if the filter is not subjected to a surface treatment, and therefore, micromanipulation by a glass capillary on the filter is easy (FIG. 4B). Therefore, the metal filter 17 of the present embodiment has the excellent advantage of being able to be applied immediately to the automation of single cell sorting.

The shape of the metal filter 17 is not particularly limited provided that it can be disposed in a filter ring (cassette) that is set in the filter unit of a CTC isolating device, and includes, for example, shapes such as round, square and the like, and is preferably round. Further, the size of the metal filter 17 can be determined appropriately in consideration of physical factors such as the amount of the sample (blood), the pore diameter, time, flow velocity, pressure and the like, and operability and cost and the like. For example, in a case of processing 5 mL of blood, the diameter (in the case of being round), or the vertical and horizontal lengths (in the case of being square), are usually around from 10 to 15 mm. However, the size can be made to be in a range of, non-restrictively for example, around from 5 to 20 mm, in accordance with the amount of blood. Further, the thickness of the metal filter 17 can be determined appropriately in consideration of the relationships with pore density, withstand pressure, cost and the like, and usually is from 10 to 40 μm, and preferably is from 15 to 40 μm.

Figure 2A:
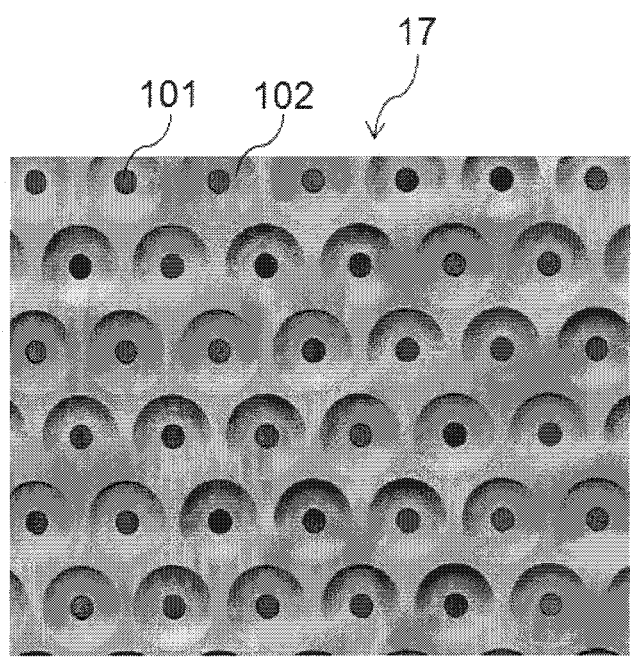
FIG. 2A is an SEM image of a 3D Pd/Ni filter. Depression diameter 30 μm, depression depth 10 μm, pore diameter 8 μm, pore density 99,178/cm² (ultra-high pore density), staggered lattice array.
Figure 2B:
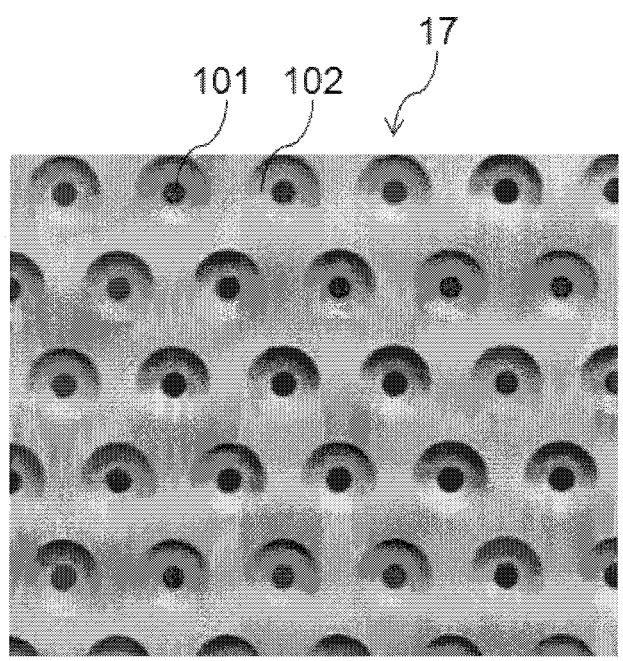
FIG. 2B is an SEM image of a 3D Pd/Ni filter. Depression diameter 30 μm, depression depth 10 μm, pore diameter 8 μm, pore density 71,656/cm² (ultra-high pore density), staggered lattice array.
Figure 2C:
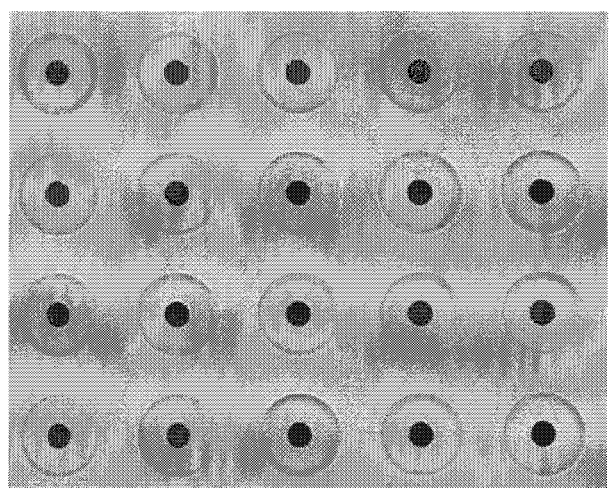
FIG. 2C is an SEM image of a 2D Pd/Ni filter. Depression diameter 30 μm, depression depth 1 μm, pore diameter 8 μm, pore density 40,000/cm², lattice array.
Figure 2D:
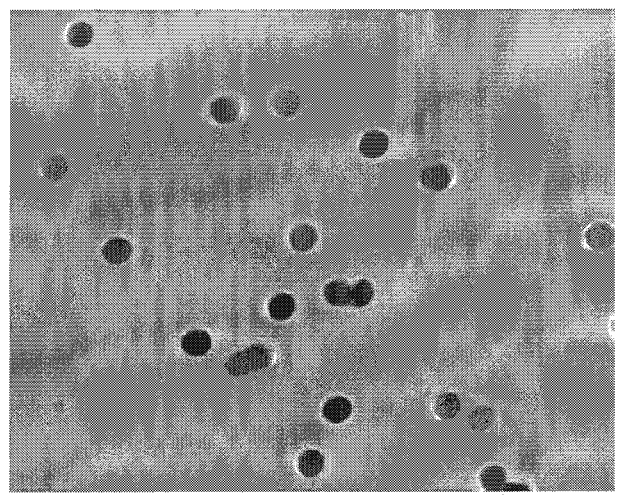
FIG. 2D is an SEM image of a commercially available polycarbonate filter (pore diameter 8 μm, Whatman Co.).
Figure 2E:
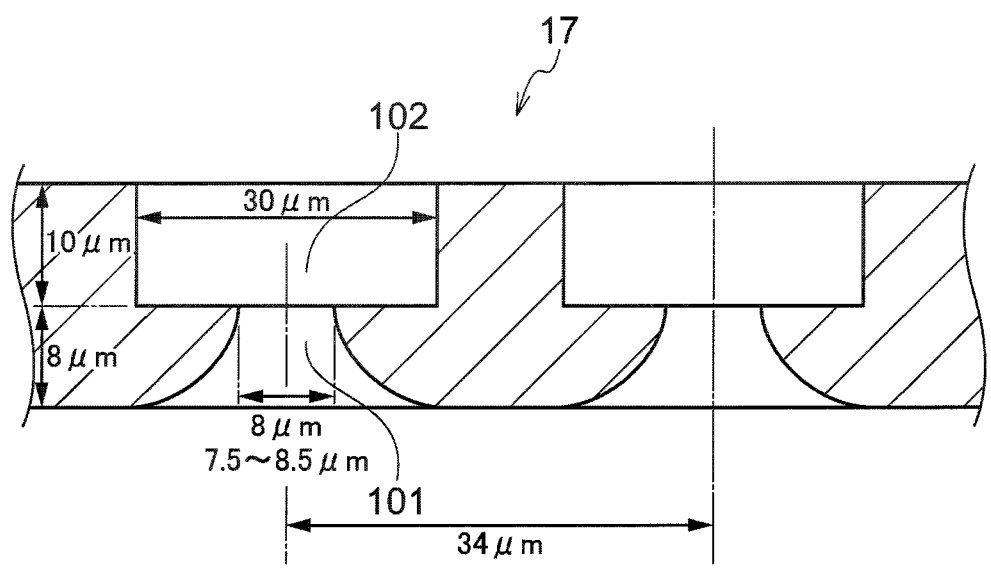
FIG. 2E is a cross-sectional view schematically showing the metal filter shown in FIG. 2A.

As shown in FIG. 2A, FIG. 2B and FIG. 2E, the metal filter 17 has a large number of pores 101 that are arranged uniformly and regularly. These pores 101 are formed in depressions 102 that are described later. The density of the pores 101 per 1 cm² of filter surface area differs in accordance with the form of the array such as a lattice array, a staggered array, or the like, but is usually from $1\times10^4$ to $2\times10^5/cm^2$, and is preferably from $5\times10^4$ to $1\times10^5/cm^2$. Further, the pore diameter of the pore 101 is a size that is such that CTCs or rare cells cannot pass therethrough, and body fluid cells other than CTCs or rare cells, such as blood components such as blood cells or the like, can pass therethrough. As a result of histogram analysis, the sizes (long diameter) of human blood cell components are around from 6 to 7 μm for red blood cells, around from 7 to 9 μm for white blood cells, and less than 5 μm for platelets, whereas the size is around from 10 to 20 μm for CTCs or rare cells. Accordingly, the pore diameter at the position where the pore 101 opens to the depression 102 is usually around from 7 to 10 μm, and is preferably around from 7.5 to 9 μm, and is more preferably around from 7.5 to 8.5 μm.

The metal filter 17 further has the depressions 102 (or recesses) that are of sizes such that they can capture CTCs or rare cells. It suffices for the size of the depressions 102 to be a size such that CTCs or rare cells can be captured, and is, non-restrictively, for example, a diameter of from 20 to 30 μm and a depth of from 5 to 15 μm, and preferably, a diameter of from 25 to 30 μm and a depth of 10 μm. The above-described depressions 102 may be formed at the upper portions of all of or some of the above-described pores 101, and, in order to maintain a high pore density, such a form is preferable. If the depth is less than 5 μm, CTCs will not be able to enter therein. In order for CTCs to substantially completely enter therein, a depth of at least around from 5 to 15 μm is needed. The number of such depressions 102 is, with respect to the number of the pores 101, preferably from 80 to 100%, and is more preferably 100% (i.e., the depressions 102 exist at the upper portions of all of the pores 101).

The pores 101 being "arranged regularly" at the metal filter 17 means that the pores 101 are arranged so as to be as high density as possible, and all of the pores 101 are arrayed so as to have a specific regularity. For example, an array in the form of a lattice, a staggered lattice array, a radial array, an array in the form of concentric circles, and the like (FIG. 2A, FIG. 2B, and FIG. 2C) are encompassed by this regularity. In FIG. 2A and FIG. 2B (staggered lattice arrays), the depressions 102 of a depth of 10 μm are formed at the upper portions of the pores 101, and there is a 3D structure on the whole, and therefore, in the present specification, a filter of such a form is called a 3D filter. On the other hand, in FIG. 2C (a lattice array), depressions of a depth of 1 μm exist at the upper portions of the pores 101, but there is a structure that is close to planar overall, and therefore, in the present specification, a filter of such a form in which the depth of the depressions is less than 5 μm is called a 2D filter. This 2D filter corresponds to the size-selective microcavity array that is disclosed in FIG. 5 of JP-A No. 2011-163830. The depressions of this 2D filter are too shallow with respect to the size of CTCs or rare cells, and therefore, the CTCs or rare cells that are captured by these pores cannot be segregated from the surrounding, remaining blood cells. In contrast, the metal filter 17 of the present embodiment is a 3D filter. By providing the depressions 102, single cell picking by manipulation and that is accurate and simple and gentle becomes possible (FIG. 4A) for reasons such as 1) the CTCs can be arrayed (patterned) one-by-one without contamination of blood cells, and 2) the strength at which the cells are captured in the pores 101 can be controlled by utilizing the flow, that arises under a given condition and that is in the opposite direction of gravity, and optimizing the balance with the water pressure, and the like. However, when the depth of the depressions 102 is deep (exceeds 15 μm), although there is no effect on the recovery rate and the filtering speed of CTCs, conversely, drawbacks such as single cell patterning being incomplete, and resistance arising at the time of picking, and the like can arise.

It is preferable that the peripheral edge of the metal filter 17 is hemmed without pores. Due to the existence of an edge portion, the CTC measurement is accurate, and further, the metal filter 17 can be pinched by forceps without being damaged. Further, there are cases in which, depending on the conditions of the electroforming, slight warping arises at the metal filter 17 due to the provision of the depressions 102. However, if the support material such as polycarbonate or the like is hemmed from above and below by ultrasonic welding or the like, correction of warping is possible.

The metal filter 17 of the present embodiment can be fabricated by utilizing, for example, the LIGA (Lithogaphie Galvanoformung Abfomung) technique (Tadashi Hattori, Hyomen Gijutsu (Surface Techniques), Vol. 62, No. 12, 619-624, 2011; W. Elufeld and H. Lhe, Radiat. Phys. Chem., 45(3): 340-365, 1995). As one example, an electroformed filter can be fabricated (see FIG. 8A through FIG. 8F) by a method including layering a resist, an absorption material (an arbitrary component), and a mask on a substrate, and forming a resist pattern by irradiating ultraviolet rays, X-rays or synchrotron radiation, and thereafter, carrying out metal plating in which electroforming is carried out by using the substrate as an electrode, and finishing the electroforming when predetermined openings remain, and further, carrying out resist removal.

2. Device for Isolating Periphery Circulating Tumor Cells (CTCs) or Rare Cells

The present embodiment further provides a device that is for isolating CTCs or rare cells from a body fluid such as blood or the like, and that is characterized by having the porous metal filter 17.

The metal filter 17 that is porous is as described in above section 1. A filter that is preferable from the standpoints of cost and the like is a palladium (Pd) filter or a palladium (Pd)/nickel (Ni) alloy filter.

In the device of the present embodiment, this metal filter 17 is set such that the flow path becomes perpendicular with respect to the metal filter 17. Usually, the metal filter 17 is set removably or irremovably with respect to a filter cassette 16, and this filter cassette 16 is fixed to the device. The filter cassette 16 is structured by two members that are upper and lower members (a filter ring upper and a filter ring lower) that have edges having a width that is suitable for fixing the metal filter 17 and whose inner sides are open spaces, and the metal filter 17 is fixed between these members. As needed, packing (e.g., Teflon®, rubber, paper, or the like) may be sandwiched between the members and the metal filter 17, and due thereto, deformation of the metal filter 17 and leaking of fluid can be prevented (FIG. 3B through FIG. 3C). The member that is the filter cassette 16 is formed from a material such as a resin (polymer), rubber, metal or the like, and means for fixing the filter are provided at the two members. For example, screw grooves or the like are an example of such means. Or, the filter cassette 16 may be a structure in which the metal filter 17 is fixed (press-fit) merely by pressure from above and below. Or, the filter cassette 16 may be fabricated such that the metal filter 17 and the filter cassette 16 are integral, and, in this case, the metal filter 17 is fixed to the filter cassette 16 so as to be unable to be removed therefrom.

Figure 3A:
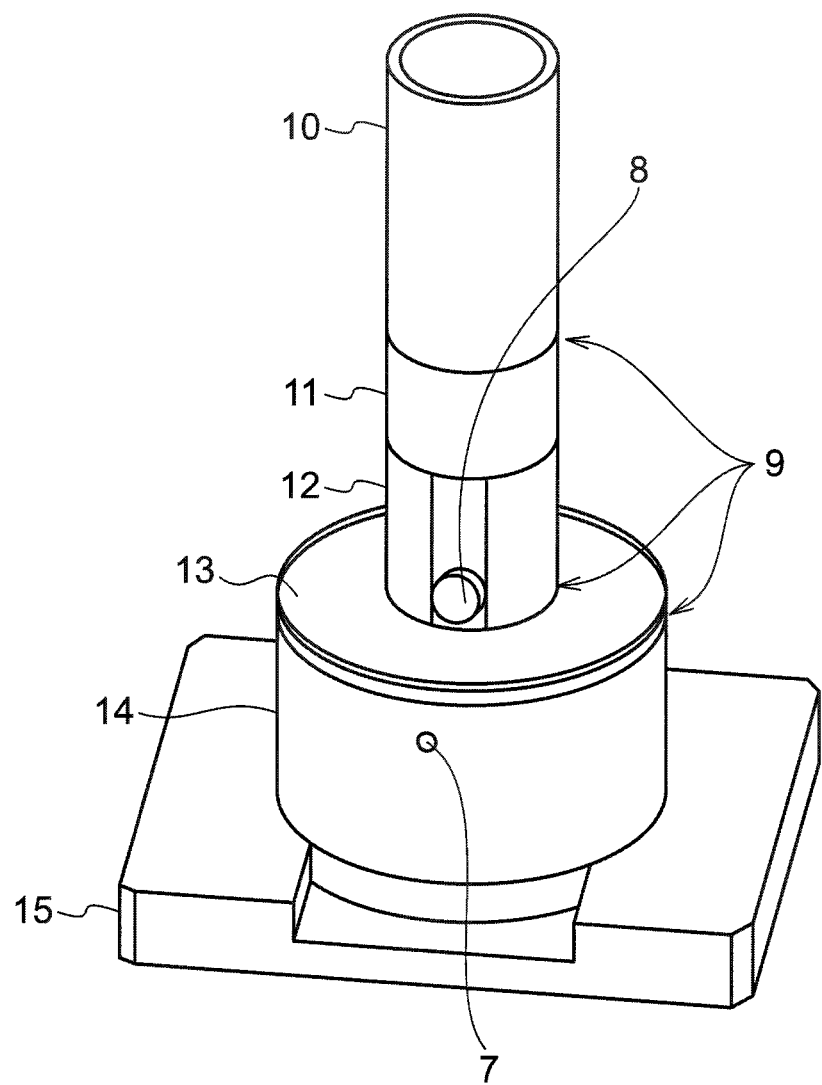
FIG. 3A is a schematic drawing of the exterior of a device. The device has, for example, a width of 15 cm, a depth of 12 cm, and a height of 22 cm.
Figure 3B:
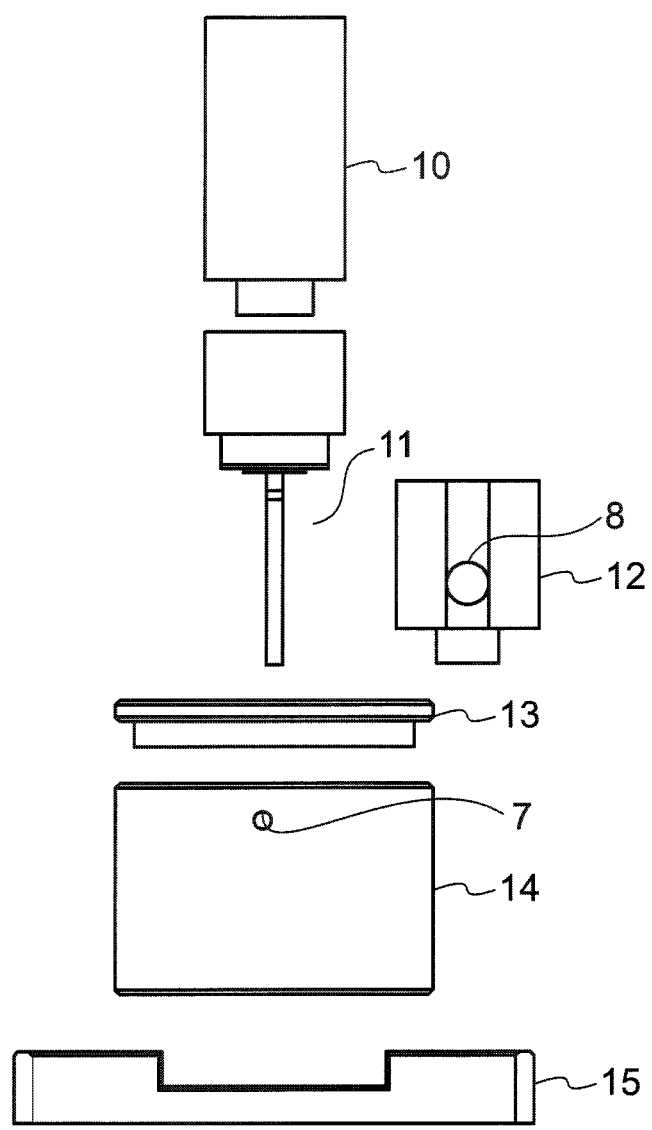
FIG. 3B is a schematic drawing of structural parts of the device.
Figure 3C:
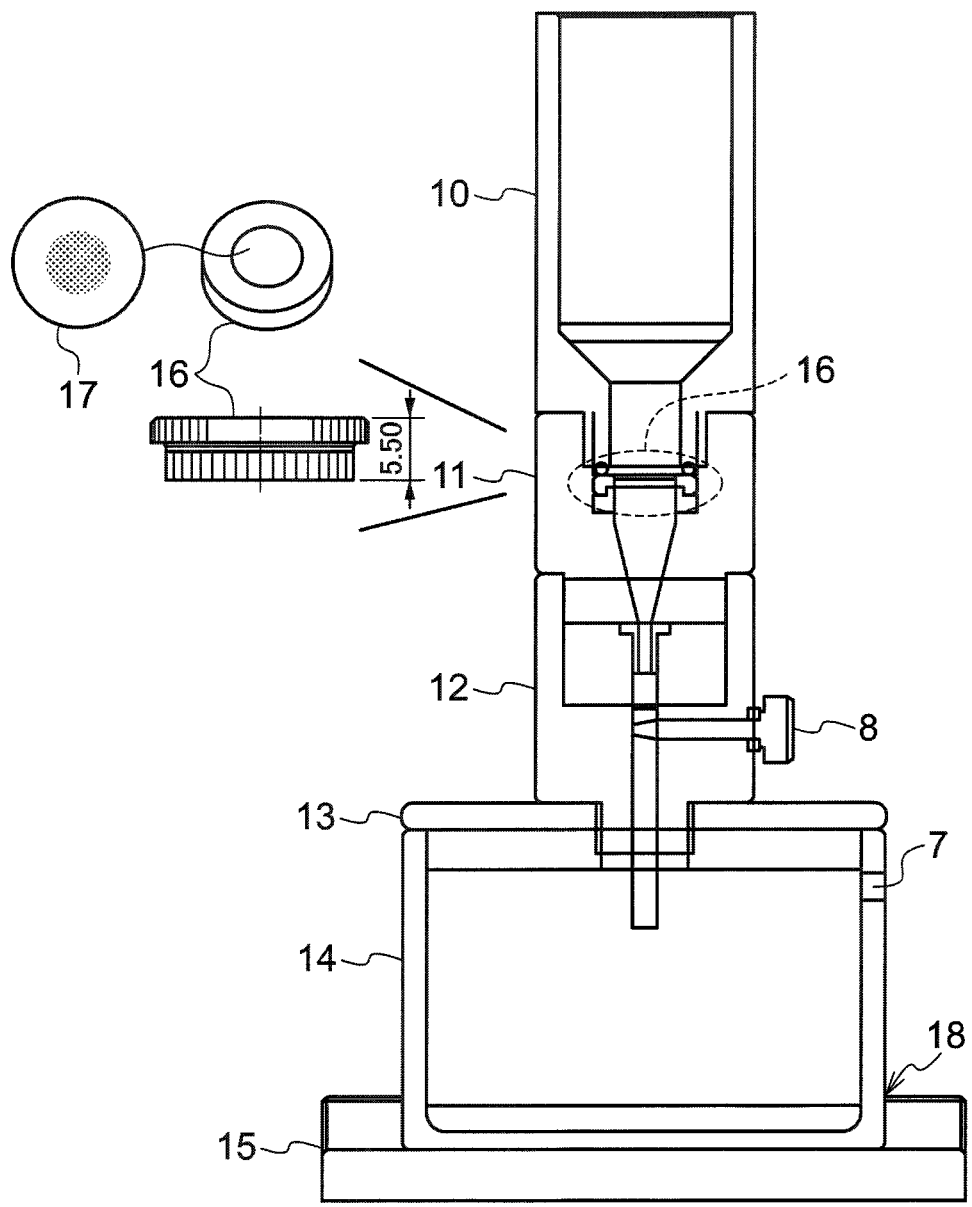
FIG. 3C is a front view schematically showing the device in which respective units are assembled together.

In addition to a filter unit 11 that includes the filter cassette 16 in which the metal filter 17 is set, the device can further include a reservoir unit 10, a flow amount regulating unit 12, and a drainage recovery unit 14 (liquid storing base) (FIG. 3A).

The reservoir unit 10 is a container in which a body fluid sample such as blood or the like is placed, and is formed from a material that is such that the liquid surface can be discerned (e.g., that is transparent) such as glass or a polymer or the like, and, as needed, may have liquid amount (e.g., measurement) graduations.

The filter unit 11 is as described above, and includes the filter cassette 16 that is for removably setting the metal filter 17.

The flow amount regulating unit 12 has a device for regulating the flow amount or the flow velocity of the body fluid such as blood or the like that flows down naturally due to its own weight (i.e., gravity) through the reservoir unit 10 and the filter unit 11 that includes the filter cassette 16. Such a device is, for example, a screw-in-type convex screw having a distal end that has an acute angle structure, and, when the screw is tightened, a waste liquid tube is compressed and the flow amount decreases or becomes zero (stops), whereas on the other hand, when the screw is loosened, the flow amount increases. The screw is formed from a material such as, for example, a metal, a resin, a polymer or the like.

The drainage recovery unit 14 includes a container (a liquid storing base) that recovers the body fluid such as blood or the like after having been filtered, and drainage when the device is washed, and the like. This drainage recovery unit 14 is formed from a material such as, for example, glass, a resin, a polymer, a metal or the like.

With regard to the fixing together of the respective units, for example, the units may be fixed by utilizing screw mechanisms 9 (FIG. 3A) at which mounting and removal are carried out by rotating, or the fixing may be carried out by an insertion-type gap fit-in portion 18 (FIG. 3C), or may be carried out another common fixing tool. Moreover, in addition to the above-described respective units, a stand for setting of the structural body in which the units have been assembled together can be provided.

Examples of the device are shown in FIG. 3A (the exterior), FIG. 3B (structural parts), and FIG. 3C (a front view of the device when assembled). In the drawings, the filter unit 11 includes the filter cassette 16. The flow amount regulating unit 12 includes a liquid amount regulating screw 8. At the drainage recovery unit 14, a liquid storing lid 13 is provided at the top surface thereof, and an air hole 7 is provided in the upper portion of a side surface thereof. A stand 15 is further included in the device.

From the standpoints of ease of machining and cost, it is preferable that the entire device be formed of a resin or a polymer that is acrylic or the like. A transparent material is preferable because the flow-down velocity of the liquid can be observed. The size of the device, as the assembled structural body excluding the stand 15, is a lateral width of around from 10 to 15 cm and a height of around from 20 to 30 cm, and is a size that is suitable for filtering a blood sample of around from 5 to 7.5 mL. However, even cases in which the volume of the sample is large can be sufficiently addressed by this size by dividing the sample into smaller portions and applying them to the device.

Note that the above are specifications of a prototype. For a mass-produced-type, separately, a mold is fabricated on the basis of this prototype, and the device is fabricated by using a material such as resin or plastic or the like for example. Therefore, the production of a low-cost, disposable device is possible.

The device of the present embodiment is a pumpless system (i.e., a system that does not utilize a pump) that can obtain a flow velocity for filtering by the weight of the sample (gravity), and accordingly, is a free system. This is different from the driving force of a pump system or a negative pressure tube system that are employed in publicly-known filter-type CTC isolating devices. In these conventional systems, there are problems such as stress is applied to the cells, and single cell sorting of living cells is difficult because of the fixing of the cells or the closed nature of the flow path, and the like. However, in the device of the present embodiment, such problems can be overcome.

With the device of the present embodiment, due to the application of palladium or the like, that has extremely low toxicity with respect to cells, to the metal filter 17, and the ultra-high pore density of the metal filter 17, and flat surface machining, and making the metal filter 17 be 3D, high-speed filtering of blood cells, while keeping the flow velocity at which CTCs or rare cells are captured in the pores 101 at a relatively low speed, is made possible even without a pre-treatment of the body fluid such as blood or the like. Concretely, although high-speed filtering of 5 mL of whole blood for around 30 minutes including washing is possible, the flow velocity of passage through the pores 101 is relatively slow. Further, because the pores 101 have an extremely smooth surface characteristic, the stress and damage applied to the cells are low.

As a result, CTCs or rare cells can be aligned in a state in which there is little contamination of the blood cells and the like. Moreover, by providing the depressions 102 above the pores 101, it is thought that flow in the direction opposite gravity will arise rheologically under a given condition. Therefore, CTCs are not captured deeply in the pores 101, and accordingly, the shearing stress that is applied to the CTCs can be kept to a minimum. Therefore, cytotoxicity to CTCs or rare cells can be kept to a minimum, and CTCs or rare cells can be isolated at a survival rate of approximately 100% and a recovery rate of around 80% or more.

3. Method of Isolating Periphery Circulating Tumor Cells (CTCs) or Rare Cells

The present embodiment further provides a method of isolating CTCs or rare cells from a body fluid of a cancer patient by using the device in which the above-described metal filter 17 is set.

Concretely, this method is a method of isolating CTCs or rare cells from a body fluid, and includes injecting a body fluid, that is selected from blood, stomach fluid, peritoneal washing fluid, spinal fluid or lymph fluid for example, of a cancer patient into the device of the present embodiment, and isolating CTCs or rare cells at the upper portion of the metal filter 17 at a flow velocity that relies only on gravity.

The body fluid of the cancer patient that serves as the specimen is a body fluid that contains CTCs or rare cells or is suspected to contain CTCs or rare cells, and is mainly blood or lymph fluid.

The amount (volume) of the body fluid that is used in isolating CTCs or rare cells is usually from 1 to 20 mL, and preferably from 3 to 7 mL. Usually, the body fluid (blood in particular) is filtered after having been diluted from 2 to 20 times for example by phosphate buffered saline (PBS) (PBS containing from 0.25 to 1 mM EDTA in accordance with the object). In particular, in cases in which the amount of blood is large or there is a large number of blood cells, the following pre-treatment may be carried out.

Figure 5A:
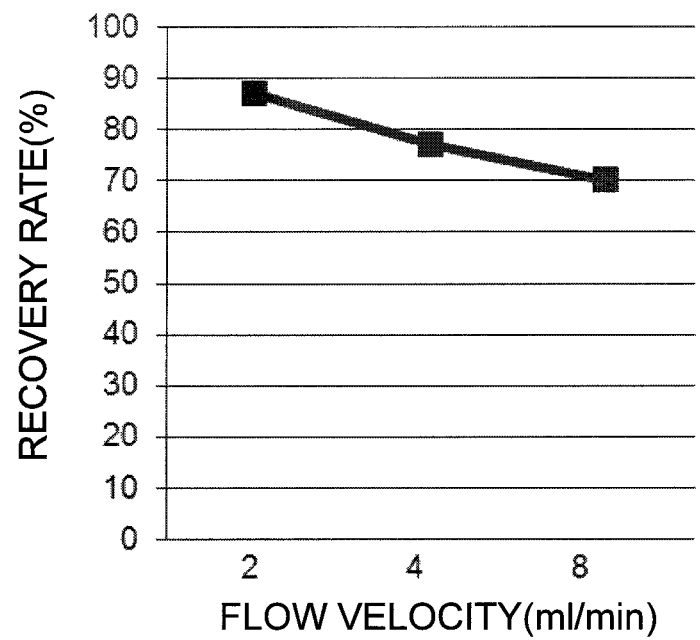
FIG. 5A A sample, that was prepared by mixing 500 cultured cancer cells (COLM5-EGFP) in 2.5 mL of healthy human blood and diluting the mixture 10 times by PBS, was filtered by using a 3D Pd/Ni filter, and the recovery rate (%) of cancer cells was investigated while varying the flow velocity of the device.
Figure 5B:
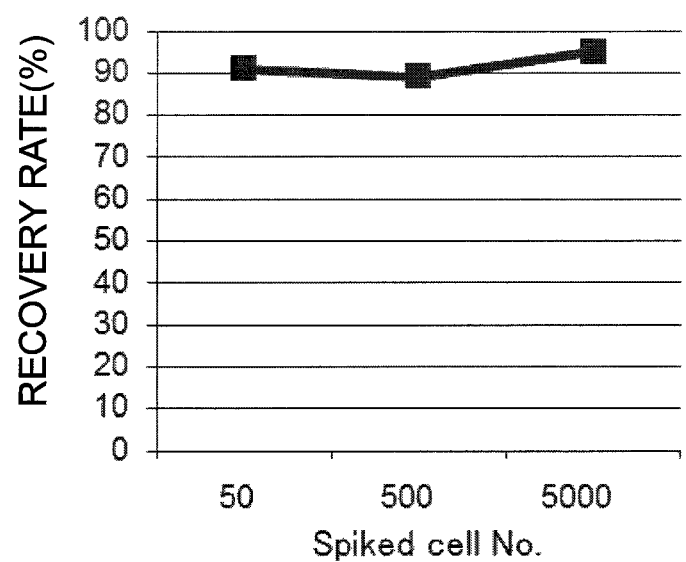
FIG. 5B A sample, that was prepared by mixing cultured cancer cells (COLM5-EGFP) in 2.5 mL of healthy human blood and diluting the mixture 10 times by PBS, was filtered by using a 3D Pd/Ni filter, and the recovery rate (%) of cancer cells was investigated while varying the number of cancer cells. The flow velocity of the device is 2 ml/min.

This pre-treatment includes, for example, mixing a body fluid together with cationic liposomes (MCL) that contain magnetic nanoparticles, and causing these magnetic nanoparticles to be taken into the CTCs or the rare cells and the white blood cells within the body fluid, and thereafter, making the mixture flow into a flow path that passes through the metal filter 17 of the present embodiment, and removing, in advance from this body fluid, the red blood cells and the like that were located in the midst of the flow path and were not magnetized by the magnets (pre-filtering). This utilizes the property that magnetic nanoparticles are not taken into red blood cells, whereas on the other hand, magnetic nanoparticles are taken into CTCs or rare cells and white blood cells. By removing the red blood cells through this pre-filtering and cancelling the magnetism and leading the CTCs or the rare cells and the white blood cells to the present filter device, white blood cells can be removed in a state in which the flow velocity of the metal filter 17 is slowed greatly. Therefore, CTCs or rare cells remain in the depressions 102 of the metal filter 17 without being strongly captured in the pores 101. In the case of utilizing both such a pre-treatment and processing by the metal filter 17 of the present embodiment, as compared with a case of carrying out processing by the metal filter 17 alone, shearing stress that is applied to the CTCs or the rare cells is reduced, and the CTCs or rare cells can be recovered at a higher recovery rate (from 80 to 90%) (FIG. 5A, FIG. 5B).

The present method is a simple method in which a body fluid is injected into the device and filtering is carried out at a flow velocity due to gravity. However, by using the 3D metal filter 17 that has an ultra-high pore density (e.g., from $5 \times 10^4$ to $1.5 \times 10^5/cm^2$), allowable and sufficient high-speed processing can be achieved. For example, around 5.0 mL of a specimen (whole blood) can be processed in around 30 minutes including washing. Phosphate buffered saline (PBS) is used as the washing liquid, but may contain EDTA as needed.

Next, in order to measure the number of CTCs or rare cells on the metal filter 17, the CTCs or rare cells are stained by using a fluorescent labeled antibody that specifically binds to CTCs or rare cells, e.g., an antibody mixture of Alexa 488 labeled anti-EpCAM antibody and PE-labeled anti-CD45 antibody that specifically binds to white blood cells, or the like, and the number and the like of the CTCs or rare cells is measured by a microscope. The staining at this time can be carried out directly on the metal filter 17 that is fixed to the device.

After staining, the filter cassette 16 is removed from the device, and the number of CTCs is counted while in the filter cassette 16 as is under an upright fluorescence microscope, and moreover, the CTCs or rare cells can be recovered one-by-one from the depressions 102 of the metal filter 17 by using a manipulator formed from a minute glass capillary. Further, the FISH method that investigates the presence of gene amplification can be carried out by removing the metal filter 17 from the filter cassette 16 and fixing it as is.

Figure 6A:
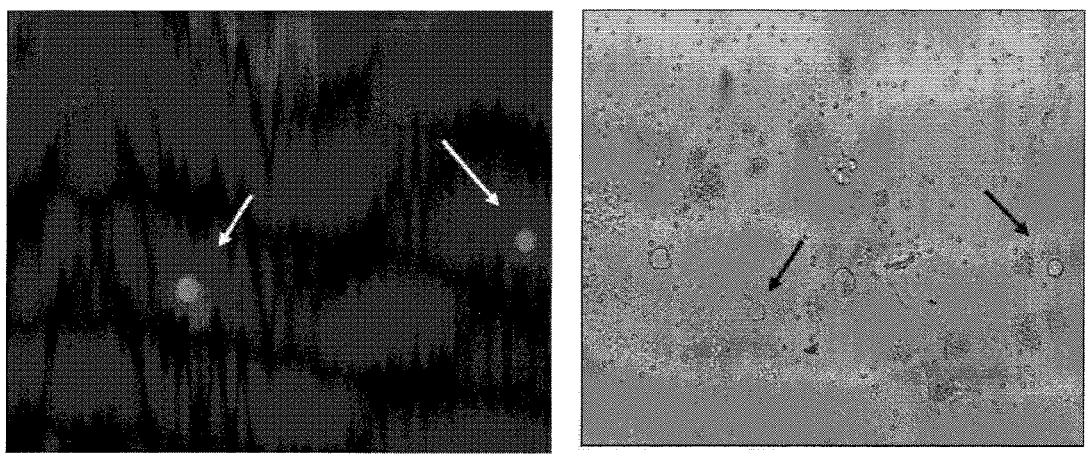
FIG. 6A Blood that was drawn three months after transplantation from a nude mouse in which cultured cancer cells (COLM5-EGFP) were subcutaneously transplanted was filtered by a 3D Pd/Ni filter, and the GFP fluorescence was observed. The left side is a GFP fluorescence image, and the right side is a bright field image. The arrows are CTCs.
Figure 6B:
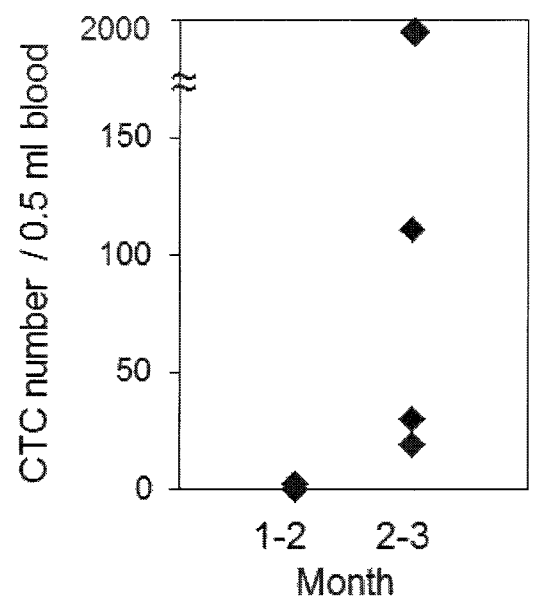
FIG. 6B Blood that was drawn from 1 to 2 months after and from 2 to 3 months after transplantation from a nude mouse in which cultured cancer cells (COLM5-EGFP) were subcutaneously transplanted was filtered by a 3D Pd/Ni filter, and the number of CTCs was measured.

Further, the 3D Pd/Ni metal filter device of the present embodiment can also be used in the measurement of CTCs in peripheral blood of tumor-bearing mice. The present inventors created plural lines of CTC models (mice) that can detect CTCs with good reproducibility, by using a subcutaneous transplantation and spontaneous metastasis model of GFP-introduced colon cancer cell lines (COLM5-EGFP) or stomach cancer cell lines (GCIY-EGFP) or the like. Caudal vena cava blood of the mouse from 1 to 3 months after transplantation was drawn, and filtering was carried out by the 3D Pd/Ni alloy filter device of the present embodiment, and the number of CTCs was measured by using GFP fluorescence as the index. As a result, it was confirmed that CTCs were detected within the mouse blood, in correlation with the extent of metastasis (FIG. 6A, FIG. 6B). Moreover, RNA and DNA were extracted from several of the recovered CTCs, and it was confirmed that the expression and genetic mutations of specific genes could be analyzed.

Moreover, even with actual clinical specimens (peripheral blood) of breast cancer patients and stomach cancer patients and the like, when filtering was carried out by the 3D Pd/Ni alloy filter device of the present embodiment and the number of CTCs after CTC staining was measured, in the same way as the mouse CTC models, a significantly large number of CTCs was detected and the efficacy in clinical specimens of the present embodiment also was confirmed (FIG. 7A, FIG. 7B, FIG. 7C) in metastatic patient specimens as compared with the blood of healthy persons.

From the above, it can be anticipated that the method of the present embodiment will from here on play an important role in both diagnoses and ways of treating metastatic cancers, such as in early diagnosis of recurrence of metastases, companion diagnostics, evaluation of therapeutic effects of medications, and the like. Further, it is expected that the device and method of the present embodiment will be greatly useful in basic research such as the elucidation of metastatic mechanisms such as the dynamics of CTCs within living bodies.

EXAMPLES

The present embodiment is described in further detail by way of illustration of the following Examples. However, the technical scope of the present embodiment is not limited by these concrete examples.

Example 1

[Method of Fabricating Palladium/Nickel Filter]

Figure 8A:
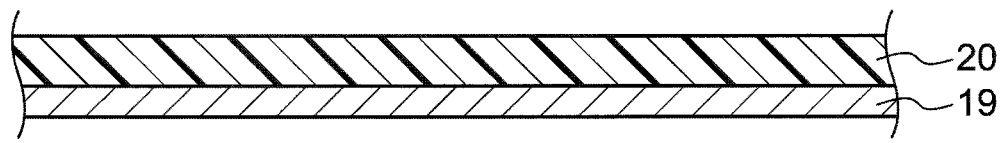
FIG. 8A is a schematic drawing explaining a method of fabricating a palladium/nickel filter using lithography by X-rays or ultraviolet rays, and electroforming.

As shown in FIG. 8A, a photosensitive resist 20 was coated to a predetermined thickness on a substrate 19. Note that, in a case of using a silicon substrate or a glass substrate that is not electrically conductive as the substrate 19, an electrically conductive film layer (e.g., copper) is added, but the substrate 19 may be electrically conductive such as a stainless steel substrate, a nickel substrate, a copper substrate, or the like.

Figure 8B:
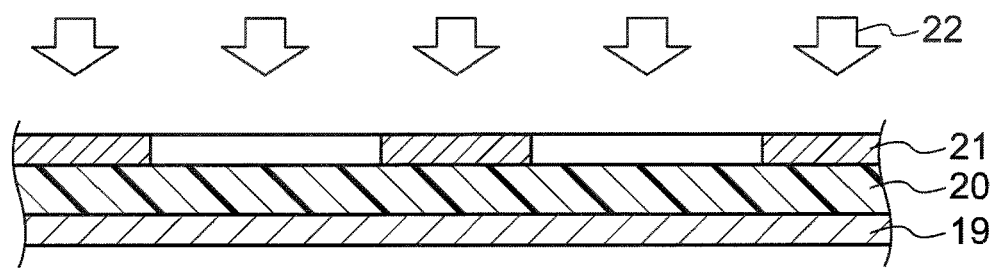
FIG. 8B is a schematic drawing explaining the method of fabricating a palladium/nickel filter using lithography by X-rays or ultraviolet rays, and electroforming.

Next, as shown in FIG. 8B, exposure was carried out by irradiating ultraviolet rays 22 via a Cr mask 21 on which a predetermined pattern was drawn. Here, in a case in which X-rays are used as the light source instead of the ultraviolet rays 22, an X-ray mask is used instead of the Cr mask 21.

Figure 8C:
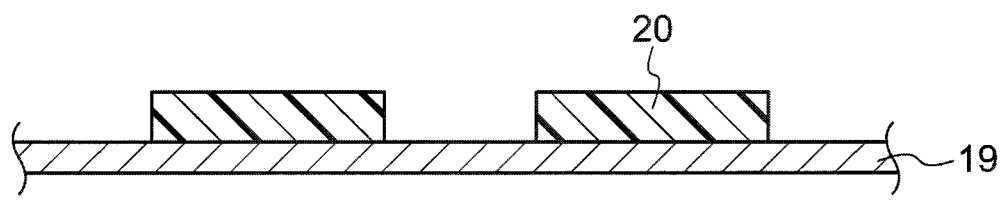
FIG. 8C is a schematic drawing explaining the method of fabricating a palladium/nickel filter using lithography by X-rays or ultraviolet rays, and electroforming.

Next, as shown in FIG. 8C, a photosensitive resist 20 was patterned on the substrate 19 by undergoing a development process.

Figure 8D:
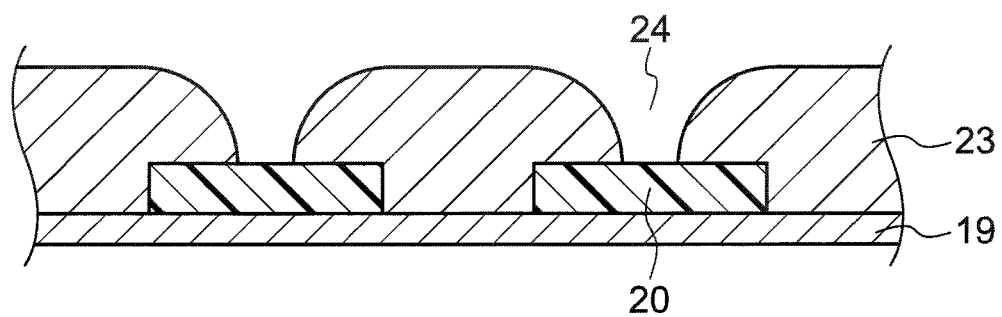
FIG. 8D is a schematic drawing explaining the method of fabricating a palladium/nickel filter using lithography by X-rays or ultraviolet rays, and electroforming.

Next, as shown in FIG. 8D, a deposited film 23 of a palladium/nickel alloy (Pd/Ni) (with the Pd:Ni weight ratio being 80:20 for example) was deposited by electroforming from the obverse of the substrate 19. Deposition of the Pd/Ni deposited film 23 by electroforming was carried out continuously so as to cover the patterned photosensitive resist 20, and, when predetermined openings 24 remained, the electroforming was ended.

Figure 8E:
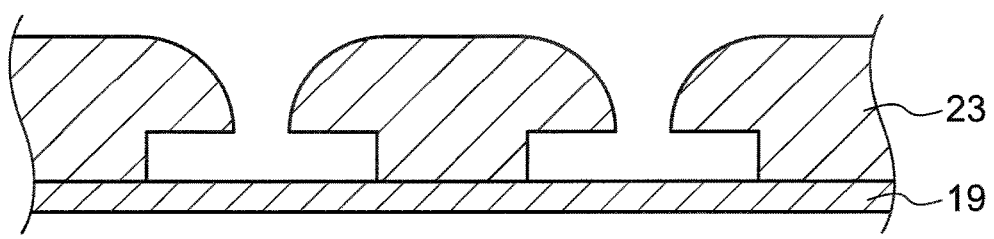
FIG. 8E is a schematic drawing explaining the method of fabricating a palladium/nickel filter using lithography by X-rays or ultraviolet rays, and electroforming.

Next, as shown in FIG. 8E, the formed photosensitive resist 20 was removed by an organic solvent. Dry etching by oxygen plasma may be utilized in this removal of the photosensitive resist 20.

Figure 8F:
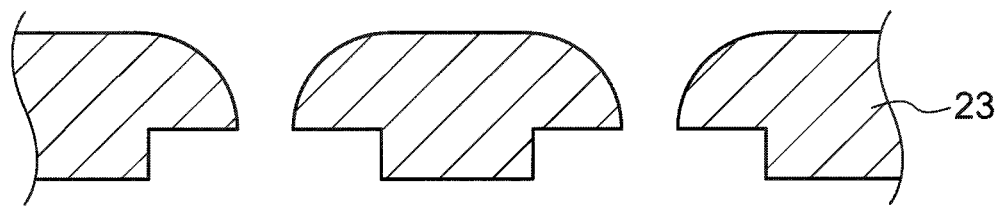
FIG. 8F is a schematic drawing explaining the method of fabricating a palladium/nickel filter using lithography by X-rays or ultraviolet rays, and electroforming.

Finally, as shown in FIG. 8F, the substrate 19 was peeled-off or was removed by etching.

Through these processes, a palladium/nickel filter (also called "3D filter" or "Pd/Ni filter") was fabricated.

Example 2

[Characterization of Palladium/Nickel Filter]

Figure 1A:
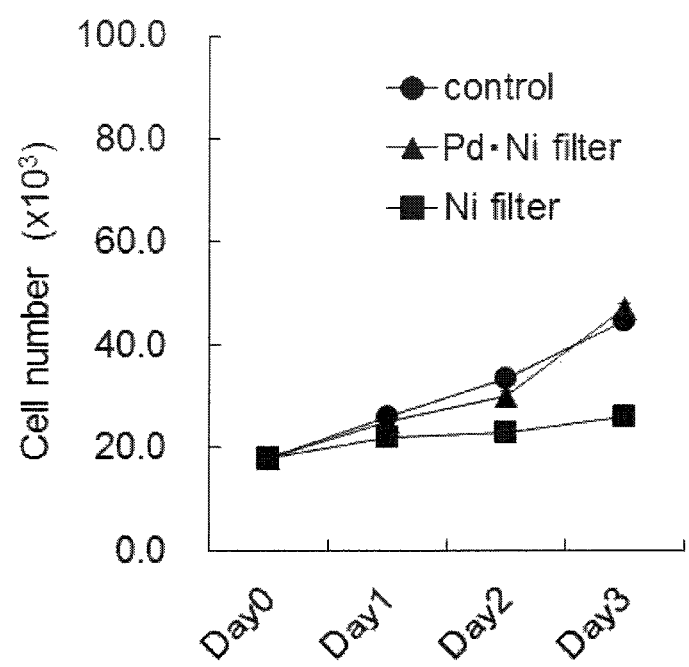
FIG. 1A MKN-45 cells were cultured for 3 days in a culture medium containing metal filter fragments, and the cytotoxicity of the metal filter was investigated. Cell proliferation curves of the control, and in the presence of a palladium (Pd)/nickel (Ni) alloy (80:20) filter, and in the presence of a nickel (Ni) filter are shown. The MKN-45 cells in the presence of the Pd/Ni filter exhibited a proliferation speed (low cytotoxicity) that was substantially the same as that of the control. The cytotoxicity of the Pd/Ni filter was clearly low as compared with that of the Ni filter.
Figure 1B:
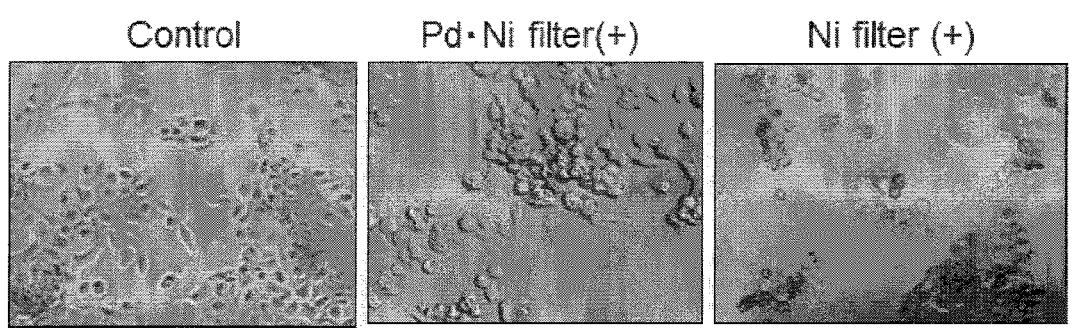
FIG. 1B MKN-45 cells were cultured for 3 days in a culture medium containing metal filter fragments, and the form of the cells was observed. The form of the cells on the third day is shown. As compared with the control and in the presence of the Pd/Ni filter, the form of the MKN-45 cells in the presence of the Ni filter was round and Apoptotic cells also were seen thereamong.

Because the present palladium/nickel filter is fabricated by fine processing by a unique and advanced electroforming technique, as compared with other filters made of polycarbonate, parylene or silicon, a high pore density of 100,000/ $cm^2$ or more and a high opening ratio of 10% or more and usually 50% or more could be achieved. Due thereto, high-speed filtering of whole blood is possible, and recovery of CTCs at a high rate and rapidly is possible without clogging (FIG. 2A and FIG. 2B). Further, highly-precise processing, such as a smooth surface characteristic and uniformity of the pores and the like, combined with the use of palladium that has low cytotoxicity as the material, can greatly reduce cytotoxicity as well (FIG. 1A, FIG. 1B).

Moreover, the present palladium/nickel filter can be subjected to a heat treatment (Autoclave) for 30 minutes at 121° C., and further, in a chemical agent resistance test (1 hour) by hypochlorous acid (a commercially available 1% Haiter) or 1N hydrochloric acid, it was confirmed that there was no change at all in the shape, and that there was no change functionally as well such as in the CTC recovery rate and the like. Due thereto, sterilization treatment is possible, and lowering of cost, such as use and reuse in the field of medical treatment and the like, can be achieved.

Example 3

[Cell Spike Test Using Cultured Cancer Cells]

Human stomach cancer cells MKN-45, GCIY and human colon cancer cells COLM-5 were inoculated in an RPMI culture medium containing 10% fetal bovine serum such that a dish of $1.0 \times 10^6$ cells/10 cm was obtained, and were statically cultured at 37° C. and in 5% $CO_2$. After from 3 to 4 days of culturing, the culture medium was removed by suction, and, after washing with PBS (pH 7.2), 0.2% trypsin/2 mM EDTA was added, and incubation was carried out for from 3 to 5 minutes at 37° C. and in 5% $CO_2$. Observing under a microscope, it was confirmed that the cells separated from the dish, and an RPMI culture medium that contained serum was added, and, after the action of the trypsin was stopped, pipetting was carried out, and cells were recovered. The recovered cells were centrifugally isolated (1200 rpm, 3 minutes), and the supernatant was removed by suction and was again suspended in a fresh RPMI culture medium. The number of living cells was counted by a dye exclusion method using trypan blue, and, after adjusting to $1 \times 10^6$ cells/ml, the solution was inoculated into a new dish.

The cell capturing (Cell Spike) test used COLM5-EGFP cells and GCIY-EGFP cells, that were cell lines in which green fluorescent protein (GFP) genes were forcibly expressed in human colon cancer cells COLM-5 and human stomach cancer cells GCIY. Using the cell suspension that was adjusted as described above, 50, 500 or 5000 cultured cancer cells were mixed together with from 2 to 2.5 ml of blood drawn from a healthy person by an EDTA 2Na-containing vacuum blood collection tube, and samples were prepared.

[Method of Isolating, and Operation of Detecting, Cultured Cancer Cells by Filter Device]

5 mL of PBS that contained 1 mM EDTA/0.5% BSA was introduced into the reservoir unit of the CTC isolating device in which the 3D filter was set, and the reservoir and the filter were washed. Thereafter, blood (from 2 to 2.5 ml), to which was added (50, 500 or 5000) GFP-introduced or non-introduced cultured cancer cells, was diluted from 5 to 10 times by PBS and was introduced. After around 10 minutes of filtering, 5 ml of PBS was introduced in order to wash the remaining blood cell components. In the case of GFP-non-introduced cultured cancer cells, after the PBS washing liquid had completely flowed-out, the liquid amount regulating screw was tightened and the flow path was closed. Thereafter, 50 µl of cell staining fluid (Alexa 488 labeled anti-EpCAM antibody, PE-labeled anti-CD45 antibody, and Hoechst 33342, each 0.5 µg/ml) was introduced. In the case of GFP-introduced cultured cancer cells, a cell staining liquid formed from the latter two was introduced. Reaction was carried out for 30 minutes at room temperature in a light-blocked state, and thereafter, the liquid amount regulating screw was loosened, and the cell staining liquid was discharged. 5 ml of PBS that contained 1 mM EDTA/0.5% BSA was introduced into the reservoir, and the cells on the filter were washed. This work was carried out one more time by using only PBS. The liquid amount regulating screw was tightened, and thereafter, the filter cassette was immediately removed from the CTC isolating device. From 100 to 200 µl of PBS was added to the liquid storage at the upper portion of the filter cassette, and the filter cassette was placed on a microscope stage, and fluorescence microscope observation was carried out as is.

In order to observe the cancer cells that were captured and recovered on the metal filter that is not light-transmissive, an upright reflection fluorescence microscope (Eclipse LV100ND; Nikon) equipped with a cooled CCD camera (Ri-1; Nikon) was used, and respective images were acquired by using a UV-1A filter, an FITC filter and a Cy3 filter, in order to observe the Hoechst 33342, Alexa 488 and PE-derived fluorescence. NIS-Elements (Nikon) was used as the image acquiring and analyzing software.

[Study of Recovery Rate of Cultured Cancer Cells Using Filter Device]

The CTC isolating device in which the 3D filter is set has the liquid amount regulating screw, and the flow velocity can be controlled by regulating the liquid amount that flows due to its own weight. Using 10-times-diluted blood (2.5 ml of blood diluted 10 times by PBS) in which 500 cultured cancer cells were mixed-together, the recovery rate in the case of changing the flow velocity to 2 ml/min, 4 ml/min, or 8 ml/min was studied. A Pd/Ni filter having a depression diameter of 30 µm, a depression depth of 10 µm, a pore diameter of 8 µm, a pore density of 99,178/$cm^2$, and a staggered lattice array was used as the 3D filter. As a result, at 2 ml/min and 4 ml/min, high recovery rates of around 90% and 80% respectively were exhibited, but at 8 ml/min, the recovery rate was 70% or less. Because it was understood that a recovery rate of from 80 to 90% can be obtained if the flow velocity is from 2 to 4 ml/min, the following experiment was carried out at a flow velocity in this range (FIG. 5A).

Next, 2.5 ml of blood was diluted 10 times by PBS, and 10, 50, 500 or 5000 cultured cancer cells were mixed-together therewith, and the recovery rate of the cancer cells was studied. The flow velocity of the device is 2 ml/min. The recovery rate from the diluted blood with which the 50, 500, 5000 cells had been mixed was from 85 to 95% (FIG. 5B). The recovery rate from the diluted blood with which only the few 10 cells had been mixed was 70%. Taking into consideration the dispersion in the count of the number of cells, this shows that there is a high recovery rate even if there is a small number of cells.

[Effects of Studying Survival Rate of Recovered Cells]

Diluted blood (2.5 ml of blood diluted 10 times with PBS), in which 5000 cultured cancer cells were mixed, was isolated by the 3D filter, and the survival rate of the captured cells was counted by a dye exclusion method using trypan blue. A Pd/Ni filter having a depression diameter of 30 µm, a depression depth of 10 µm, a pore diameter of 8 µm, and a pore density of 99,178/$cm^2$ was used as the 3D filter. The survival rate of the recovered cells was 99%, which demonstrates that this is a recovery method having extremely low cytotoxicity. However, in the case of filtering in the presence of 1 mM or more of EDTA, the proliferative property of the recovered cancer cells was significantly low as compared with the control (without EDTA being added). However, when heparin was used as an anticoagulant and adhesion was promoted by using a collagen coated dish, the proliferative property recovered significantly. Accordingly, it was thought that the decrease in the proliferative property of recovered cancer cells in the case of filtering in the presence of EDTA was due to the long-time EDTA treatment rather than stress from the filter device.

[Study of Single Cell Recovery of Cultured Cancer Cells Using 3D Filter]

A metal filter is machined into a 3D shape having depressions at the upper portions of through-holes as shown in FIG. 2A, for the purpose of improving the capturing, the aligning, and the rate of recovery of cancer cells. With regard to the shape thereof, a diameter of from 20 to 30 µm and a depth of from 5 to 15 µm are desirable, but in cases of recovering, by suction, captured cells by using a glass capillary that has been machined to a distal end diameter of around 40 µm, cells are most easily recovered when the depression diameter is 30 µm. When comparing depression depths of 5 µm and 10 µm, more so at a depth of 10 µm than at a depth of 5 µm, it is difficult for cells to move from the depressions in which they are captured even if the liquid surface moves due to manipulation or the like, and therefore, recovery, that is stable and moreover is without contamination, of the one cell that is the target is possible (a bright field image at the time of recovering one cancer cell by a manipulator is shown in FIG. 4B). When heparin was used as an anticoagulant, the adhesiveness of cells to the metal filter increased (note that cells exhibited hardly any adhesiveness at all to the metal filter in the presence of EDTA), and the recovery rate of cells by the manipulator decreased. Accordingly, it is thought that there is the need to use anticoagulants differently in accordance with the purpose.

Example 4

[Isolation of CTCs from CTC Model Mouse]

The survival environments of cells are markedly different for in vitro cultured cells and in vivo CTCs, and therefore, it is difficult to accurately evaluate the performance of a CTC isolating device merely by a Cell Spike test in which cultured cancer cells are added to healthy human blood. On the other hand, with clinical specimens of patients, evaluation of the performance of the device is difficult unless numerous cases in which the stages of the cancers differ are collected and these are measured and analyzed statistically. In contrast therewith, if there exists a mouse (hereinafter called a "CTC model mouse") in which CTCs appear with reproducibility over time after cancer cell transplantation, rapid and accurate evaluation of the performance of a CTC isolating device can be expected. Further, a CTC model mouse is extremely useful also in basic research on CTCs such as analysis of the dynamics of CTCs within living bodies, and the like.

[Creation of CTC Model Mouse and Evaluation of Filter Device Using This]

Stomach cancer cell lines (GCIY-EGFP) and colon cancer cell lines (COLM5-EGFP), that were highly metastatic and emitted green fluorescent light of a high luminance due to GFP genes being introduced, were respectively subcutaneously transplanted into nude mice. After time passed, the mice were killed, and from 0.5 to 1.0 ml of blood was drawn from the caudal vena cava and diluted 10 times by PBS, and thereafter, the CTCs were measured by the CTC isolating device. Simultaneously, the presence of micrometastases of the lungs, liver, kidneys and the like was studied by using an inverted fluorescence microscope. In the colon cancer COLM5-EGFP subcutaneous transplantation model, up to from 1 to 2 months after the transplantation, lung metastases were limited to a small number of micrometastases, and the number of CTCs also was substantially 0 (zero), and were of the extent that one to two CTCs were detected rarely. On the other hand, from 2 to 3 months after the transplantation, lung metastases were observed with the naked eye, and metastases were observed in the liver and the kidneys as well although there were small numbers thereof. At this time, around from 10 to 100 CTCs were detected, and when there were many, 1000 or more CTCs were detected (the results are shown in FIG. 6A and FIG. 6B). Also in the stomach cancer GCIY-EGFP subcutaneous transplantation model, CTCs were detected concurrently with the appearance of macroscopic metastases and metastases of the entire body. Experiments were carried out similarly by using the present device also with a lung cancer model that used mouse Lewis lung cancer cell lines (Lewis-GFP), and it was made clear that the appearance of CTCs was synchronized with metastases of multiple organs such as to the liver, the kidneys and the like. Because CTCs appeared synchronously with macroscopic metastases and metastases of the entire body, the possibility of CTC detection being useful in early diagnosis of cancer metastases is suggested. Further, from studies using CTC model mice, it is shown that the present device has sensitivity and accuracy that are sufficient to be able to accurately capture the in vivo dynamics of CTCs.

Various types of genetic analysis were carried out on CTCs that were isolated from model mice. Direct staining on a metal filter is possible with immunofluorescence staining, and in HER2-positive stomach tumor-bearing mouse CTCs, excess expression of HER2 could be detected. It was confirmed that, when genetic analysis of CTCs recovered by using a manipulator was carried out, if there are one to several CTCs, RNA and DNA extraction and amplification, analysis of gene expression of HER2 and the like by the RT-PCR method, analysis of gene sequences of K-Ras and the like by using a direct sequencing method, and the like are possible.

Example 5

[CTC Isolation from Peripheral Blood of Stomach Cancer Patients and Breast Cancer Patients]

5 ml of blood was drawn with an EDTA 2Na-containing blood collection tube from an elbow vein of 4 stomach cancer patients, 6 breast cancer patients, and 4 healthy persons. The 4 stomach cancer patients and the 6 breast cancer patients were patients hospitalized at the Aichi Cancer Center Hospital (Nagoya, Japan). The drawing of blood from the patients was carried out after being authorized by the Aichi Cancer Center Ethics Committee (Nagoya, Japan) and written informed consent was obtained from the patients.

Figure 7A:
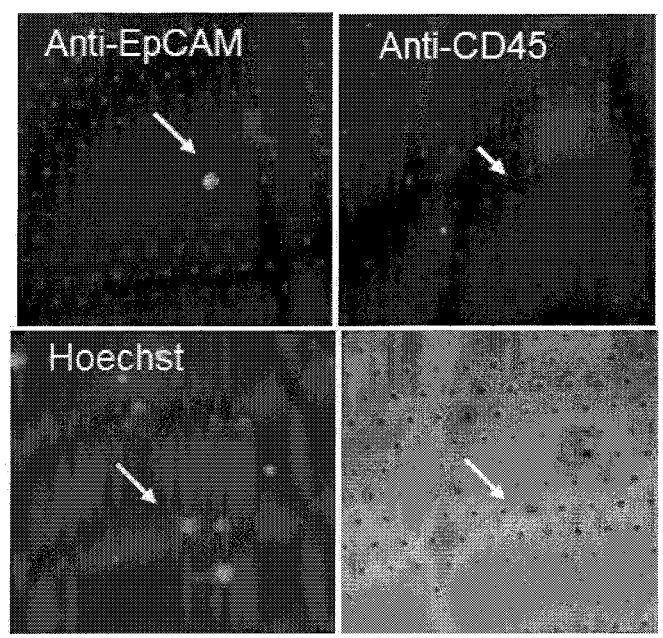
FIG. 7A Peripheral blood of a stomach cancer patient was filtered by a 3D Pd/Ni filter, and the cells were stained with a fluorescent labeled antibody. The upper left is a stain image of Alexa 488 labeled anti-EpCAM antibody, the upper right is a stain image of PE-labeled anti-CD45 antibody, the lower left is a stain image of Hoechst 33342, and the lower right is a bright field image. The arrows are CTCs.
Figure 7B:
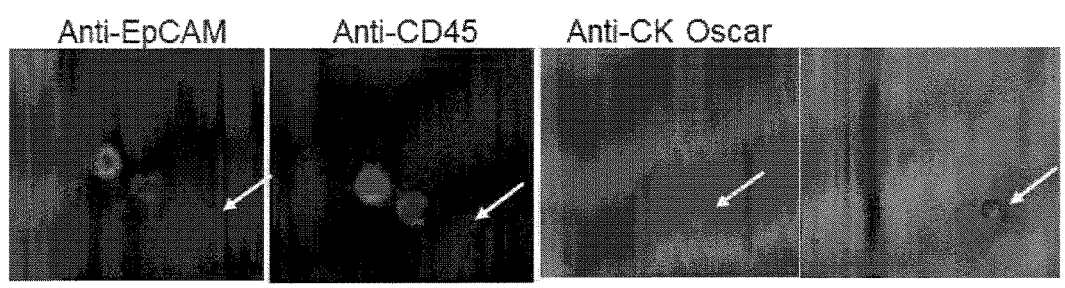
FIG. 7B Peripheral blood of a breast cancer patient was filtered by a 3D Pd/Ni filter, and the cells were stained with a fluorescent labeled antibody. In order from the left are a stain image of Alexa 488 labeled anti-EpCAM antibody, a stain image of PE-labeled anti-CD45 antibody, a stain image of Alexa 350 labeled anti-CK Oscar antibody, and a bright field image. The arrows are CTCs.
Figure 7C:
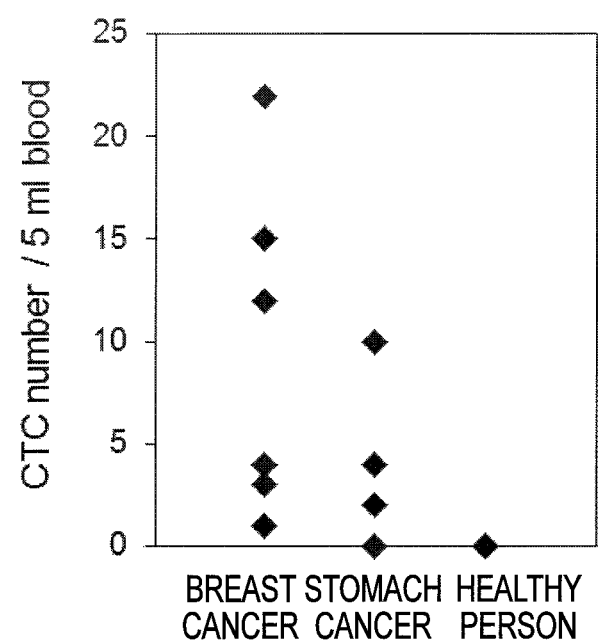
FIG. 7C The number of CTCs in 5 mL of peripheral blood of advanced breast cancer patients (6 persons), advanced stomach cancer patients (4 persons) and healthy persons (4 persons) was measured.

Within 1 hour after the drawing of blood from each person, the blood was diluted 10 times by PBS and applied to the CTC isolating device, and filtering was carried out. A 3D Pd/Ni filter having a depression diameter of 24 µm, a depression depth of 10 µm, a pore diameter of 8 µm, and a pore density of 136,325/cm$^2$ was used as the metal filter of the CTC isolating device. Filtering was carried out at a flow velocity of 2.5 ml/min. The cells on the filter cassette were washed with PBS and fixed for 10 minutes at room temperature with 10% formalin, and, after washing, a cell staining liquid containing Alexa 488 labeled anti-EpCAM antibody, PE-labeled anti-CD45 antibody, and, depending on the case, Alexa 350 labeled anti-CK Oscar antibody was added into the filter cassette, and reaction was carried out for 30 minutes at room temperature. Further, after washing with PBS, nuclear staining was carried out by Hoechst 33342. After washing with PBS, each filter cassette was moved to an upright fluorescence microscope, and the EpCAM$^+$/(CK Oscar$^+$)/CD45$^-$/Hoechst 33342$^+$ cells were judged to be CTCs, and the number of CTCs was measured. As a result, there were 0 CTCs in all of the 4 healthy persons, whereas there were 0, 2, 4, 11 CTCs respectively in the 4 advanced stomach cancer patients, and there were 1, 3, 4, 11, 15, 22 CTCs respectively in the 6 advanced breast cancer patients. Stain images of a stomach cancer patient are shown in FIG. 7A, stain images of a breast cancer patient are shown in FIG. 7B, and the results of measurement of the number of CTCs are shown in FIG. 7C.

Example 6

[Concomitant Use of Magnetic Isolation of Cells by Magnetic Nanoparticles]

By using stomach cancer cells N87, in order to aim for recovery of all CTCs, improvement of the recovery rate was attempted by concomitantly using magnetic isolation, that used magnetic nanoparticles (a pre-treatment), and isolation by size, that used the 3D Pd/Ni filter. 100 pg/cell of Magnetic Cationic Liposome (diameter 150 nm) was allowed to work for 2 hours in a cell suspension of 100 of the N87 cells, and after being mixed with bovine serum that contained 200,000 white blood cells, cells were captured by a device combining a magnetic isolating flow path and the filter. Approximately from 80 to 90% of the cells could be captured and recovered, and an improvement in the recovery rate as compared with the filter alone was recognized.

INDUSTRIAL APPLICABILITY

The device in which the metal filter of the present invention is set realizes, at a high recovery rate, the isolating of CTCs or rare cells in a body fluid such as blood or the like, and can recover CTCs or rare cells in a state near intact. Therefore, the device can be used not only in evaluating the number of CTCs, but also in genetic analysis of a single CTC cell, and there is a high possibility of the device being able to be used effectively in early diagnosis of recurrence of metastases, monitoring of therapeutic effects, liquid biopsies (body fluid biopsies), and the like.

The invention claimed is:

1. A device for isolating periphery circulating tumor cells or rare cells, comprising:
    a metal filter having depressions that can capture periphery circulating tumor cells or rare cells that are in a body fluid; and
    pores that are formed at the depressions and that can pass therethrough body fluid cells other than the periphery circulating tumor cells or the rare cells,
    wherein the metal filter is made of palladium or a palladium/nickel alloy,
    wherein a diameter of the depressions is from 20 to 30 μm, and a depth of the depressions is from 5 to 15 μm,
    wherein a diameter of the pores is from 7 to 10 μm, and
    wherein the depressions have a bottom portion and a wall portion that vertically extends around the entire bottom portion.

2. The device for isolating periphery circulating tumor cells or rare cells of claim 1, wherein a pore density of the depressions and the pores is from $1\times10^4$ to $2\times10^5$ per 1 cm$^2$.

3. The device for isolating periphery circulating tumor cells or rare cells of claim 1, wherein a thickness of the metal filter is from 10 to 40 μm.

4. The device for isolating periphery circulating tumor cells or rare cells of claim 1, comprising a filter cassette for setting of the metal filter.

5. A method of isolating periphery circulating tumor cells or rare cells, comprising:
    injecting, into the device for isolating periphery circulating tumor cells or rare cells of claim 1, a body fluid selected from blood, stomach fluid or peritoneal washing fluid of a cancer patient; and
    capturing the periphery circulating tumor cells or the rare cells that are in the body fluid in the depressions of the metal filter, and thereafter, recovering the periphery circulating tumor cells or the rare cells while living.

6. The method of isolating periphery circulating tumor cells or rare cells of claim 5, further comprising specifically staining the periphery circulating tumor cells or rare cells.

7. The method of isolating periphery circulating tumor cells or rare cells of claim 5, comprising diluting or carrying out a pre-treatment on the body fluid.

8. The method of isolating periphery circulating tumor cells or rare cells of claim 7, wherein the pre-treatment includes:
    mixing the body fluid together with cationic liposomes containing magnetic nanoparticles;
    causing the magnetic nanoparticles to be taken into the periphery circulating tumor cells or the rare cells and white blood cells that are in the body fluid; and
    thereafter, causing a mixture to flow into a flow path that passes through the metal filter, and removing, from the body fluid, cells such as red blood cells and the like that did not take-in the magnetic nanoparticles by a magnet disposed before the metal filter.

* * * * *